US008932846B2

(12) United States Patent
Horwitz et al.

(10) Patent No.: US 8,932,846 B2
(45) Date of Patent: Jan. 13, 2015

(54) UNMARKED RECOMBINANT INTRACELLULAR PATHOGEN IMMUNOGENIC COMPOSITIONS EXPRESSING HIGH LEVELS OF RECOMBINANT PROTEINS

(75) Inventors: Marcus A. Horwitz, Los Angeles, CA (US); Michael V. Tullius, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 760 days.

(21) Appl. No.: 12/664,485

(22) PCT Filed: Jun. 12, 2008

(86) PCT No.: PCT/US2008/066653
§ 371 (c)(1),
(2), (4) Date: Dec. 14, 2009

(87) PCT Pub. No.: WO2009/045575
PCT Pub. Date: Apr. 9, 2009

(65) Prior Publication Data

US 2010/0183547 A1 Jul. 22, 2010

Related U.S. Application Data

(60) Provisional application No. 60/944,051, filed on Jun. 14, 2007.

(51) Int. Cl.
*A61K 39/02* (2006.01)
*A61K 39/04* (2006.01)
*A61K 39/00* (2006.01)

(52) U.S. Cl.
CPC ........... *A61K 39/04* (2013.01); *A61K 2039/523* (2013.01)
USPC .................... 435/253.1; 435/252.3; 424/93.1; 424/93.2; 424/200.1; 424/234.1; 424/248.1; 424/278.1

(58) Field of Classification Search
USPC ................ 435/6, 7.35, 69.1, 252.8, 362, 879; 424/248.1, 190.1
See application file for complete search history.

(56) References Cited

U.S. PATENT DOCUMENTS

2006/0121054 A1 6/2006 Sun et al.
2007/0128216 A1 6/2007 Horwitz et al.

OTHER PUBLICATIONS

Chambers et al. "Identification of a *Mycobacterium bovis* BCG Auxotrophic Mutant that Protects Guinea Pigs against *M. bovis* and Hematogenous Spread of *Mycobacterium tuberculosis* without Sensitization to Tuberculin." Infection and Immunity, Dec. 2000, p. 7094-7099, vol. 68, No. 12.

Smith et al. "Characterization of Auxotrophic Mutants of *Mycobacterium tuberculosis* and Their Potential as Vaccine Candidates." Infection and Immunity, Feb. 2001, p. 1142-1150, vol. 69, No. 2.

Tullius et al. "High Extracellular Levels of Mycobacterium tuberculosis Glutamine Synthetase and Superoxide Dismutase in Actively Growing Cultures Are Due to High Expression and Extracellular Stability Rather than to a Protein-Specific Export Mechanism." Infection and Immunity, Oct. 2001, p. 6348-6363, vol. 69, No. 10.

Cole et al., "Deciphering the biology of *Mycobacterium tuberculosis* from the complete genome sequence." Nature, 1998, vol. 393, pp. 537-544, esp. p. 543, http://genolist.pasteur.fr/TubercuList/genome.cgi 15, 38.

*Primary Examiner* — Jennifer Graser
(74) *Attorney, Agent, or Firm* — K&L Gates LLP; Louis C. Cullman; Michelle Glasky Bergman

(57) ABSTRACT

Recombinant immunogenic compositions, and methods for the manufacture and use, are provided for the prevention and treatment of intracellular pathogen diseases in humans and animals. The recombinant immunogenic compositions express high levels of recombinant proteins in vectors that do not harbor an antibiotic resistance marker ("unmarked").

6 Claims, 6 Drawing Sheets

SEQUENCE LISTING

```
<160> NUMBER OF SEQ ID NOS: 17

<210> SEQ ID NO 1
<211> LENGTH: 48
<212> TYPE: PRT
<213> ORGANISM: Mycobacterium tuberculosis

<400> SEQUENCE: 1

Phe Asp Thr Arg Leu Met Arg Leu Glu Asp Glu Met Lys Glu Gly Arg
1               5                   10                  15

Tyr Glu Val Arg Ala Glu Leu Pro Gly Val Asp Pro Asp Lys Asp Val
            20                  25                  30

Asp Ile Met Val Arg Asp Gly Gln Leu Thr Ile Lys Ala Glu Arg Thr
        35                  40                  45


<210> SEQ ID NO 2
<211> LENGTH: 30
<212> TYPE: PRT
<213> ORGANISM: Mycobacterium tuberculosis

<400> SEQUENCE: 2

Ala Asp Pro Arg Leu Gln Phe Thr Ala Thr Thr Leu Ser Gly Ala Pro
1               5                   10                  15

Phe Asp Gly Ala Ser Leu Gln Gly Lys Pro Ala Val Leu Trp
            20                  25                  30


<210> SEQ ID NO 3
<211> LENGTH: 30
<212> TYPE: PRT
<213> ORGANISM: Mycobacterium tuberculosis

<400> SEQUENCE: 3

Ala Asp Pro Arg Leu Gln Phe Thr Ala Thr Thr Leu Ser Gly Ala Pro
1               5                   10                  15

Phe Asp Gly Ala Asn Leu Gln Gly Lys Pro Ala Val Leu Trp
            20                  25                  30


<210> SEQ ID NO 4
<211> LENGTH: 47
<212> TYPE: PRT
<213> ORGANISM: Mycobacterium tuberculosis
<220> FEATURE:
<221> NAME/KEY: VARIANT
<222> LOCATION: (43)..(43)
<223> OTHER INFORMATION: X = any amino acid

<400> SEQUENCE: 4

Ala Tyr Pro Ile Thr Gly Lys Leu Gly Ser Glu Leu Thr Met Thr Asp
1               5                   10                  15

Thr Val Gly Gln Val Val Leu Gly Trp Lys Val Ser Asp Leu Phe Lys
            20                  25                  30

Ser Thr Ala Val Ile Pro Gly Tyr Thr Val Xaa Glu Gln Gln Ile
        35                  40                  45
```

<210> SEQ ID NO 5
<211> LENGTH: 47
<212> TYPE: PRT
<213> ORGANISM: Mycobacterium tuberculosis
<220> FEATURE:
<221> NAME/KEY: VARIANT
<222> LOCATION: (43)..(43)
<223> OTHER INFORMATION: X = any amino acid

<400> SEQUENCE: 5

```
Ala Tyr Pro Ile Thr Gly Lys Leu Gly Ser Glu Leu Thr Met Thr Asp
1               5                   10                  15

Thr Val Gly Gln Val Val Leu Gly Trp Lys Val Ser Asp Leu Tyr Lys
            20                  25                  30

Ser Thr Ala Val Ile Pro Gly Tyr Thr Val Xaa Glu Gln Gln Ile
        35                  40                  45
```

<210> SEQ ID NO 6
<211> LENGTH: 22
<212> TYPE: PRT
<213> ORGANISM: Mycobacterium tuberculosis

<400> SEQUENCE: 6

```
Ala Glu Thr Tyr Leu Pro Asp Leu Asp Trp Asp Tyr Gly Ala Leu Glu
1               5                   10                  15

Pro His Ile Ser Gly Gln
            20
```

<210> SEQ ID NO 7
<211> LENGTH: 13
<212> TYPE: PRT
<213> ORGANISM: Mycobacterium tuberculosis
<220> FEATURE:
<221> NAME/KEY: VARIANT
<222> LOCATION: (6)..(6)
<223> OTHER INFORMATION: X = any amino acid

<400> SEQUENCE: 7

```
Ala Pro Lys Thr Tyr Xaa Glu Glu Leu Lys Gly Thr Asp
1               5                   10
```

<210> SEQ ID NO 8
<211> LENGTH: 60
<212> TYPE: PRT
<213> ORGANISM: Mycobacterium tuberculosis
<220> FEATURE:
<221> NAME/KEY: VARIANT
<222> LOCATION: (56)..(56)
<223> OTHER INFORMATION: X = any amino acid

<400> SEQUENCE: 8

```
Ala Pro Tyr Glu Asn Leu Met Val Pro Ser Pro Ser Met Gly Arg Asp
1               5                   10                  15

Ile Pro Val Ala Phe Leu Ala Gly Gly Pro His Ala Val Tyr Leu Leu
            20                  25                  30

Asp Ala Phe Asn Ala Gly Pro Asp Val Ser Asn Trp Val Thr Ala Gly
        35                  40                  45

Asn Ala Met Met Thr Leu Ala Xaa Lys Gly Ile Cys
    50                  55                  60
```

<210> SEQ ID NO 9
<211> LENGTH: 60
<212> TYPE: PRT
<213> ORGANISM: Mycobacterium tuberculosis -continued

```
<220> FEATURE:
<221> NAME/KEY: VARIANT
<222> LOCATION: (56)..(56)
<223> OTHER INFORMATION: X = any amino acid

<400> SEQUENCE: 9

Ala Pro Tyr Glu Asn Leu Met Val Pro Ser Pro Ser Met Gly Arg Asp
1               5                   10                  15

Ile Pro Val Ala Phe Leu Ala Gly Gly Pro His Ala Val Tyr Leu Leu
            20                  25                  30

Asp Ala Phe Asn Ala Gly Pro Asp Val Ser Asn Trp Val Thr Ala Gly
        35                  40                  45

Asn Ala Met Met Thr Leu Ala Xaa Lys Gly Ile Ser
    50                  55                  60


<210> SEQ ID NO 10
<211> LENGTH: 40
<212> TYPE: PRT
<213> ORGANISM: Mycobacterium tuberculosis

<400> SEQUENCE: 10

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
            20                  25                  30

Ser Pro Ala Val Tyr Leu Leu Asp
        35                  40


<210> SEQ ID NO 11
<211> LENGTH: 40
<212> TYPE: PRT
<213> ORGANISM: Mycobacterium tuberculosis
<220> FEATURE:
<221> NAME/KEY: VARIANT
<222> LOCATION: (35)..(35)
<223> OTHER INFORMATION: X = any amino acid

<400> SEQUENCE: 11

Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
            20                  25                  30

Ser Pro Xaa Leu Tyr Leu Leu Asp
        35                  40


<210> SEQ ID NO 12
<211> LENGTH: 22
<212> TYPE: PRT
<213> ORGANISM: Mycobacterium tuberculosis
<220> FEATURE:
<221> NAME/KEY: VARIANT
<222> LOCATION: (17)..(17)
<223> OTHER INFORMATION: X = any amino acid

<400> SEQUENCE: 12

Phe Ser Arg Pro Gly Leu Pro Val Glu Tyr Leu Gln Val Pro Ser Ala
1               5                   10                  15

Xaa Met Gly Arg Asp Ile
            20


<210> SEQ ID NO 13
<211> LENGTH: 30
<212> TYPE: PRT
```

-continued

```
<213> ORGANISM: Mycobacterium tuberculosis
<220> FEATURE:
<221> NAME/KEY: VARIANT
<222> LOCATION: (30)..(30)
<223> OTHER INFORMATION: X = any amino acid

<400> SEQUENCE: 13

Asp Pro Glu Pro Ala Pro Pro Val Pro Asp Asp Ala Ala Ser Pro Pro
1               5                   10                  15

Asp Asp Ala Ala Ala Pro Pro Ala Pro Ala Asp Pro Pro Xaa
            20                  25                  30


<210> SEQ ID NO 14
<211> LENGTH: 20
<212> TYPE: PRT
<213> ORGANISM: Mycobacterium tuberculosis

<400> SEQUENCE: 14

Thr Glu Lys Thr Pro Asp Asp Val Phe Lys Leu Ala Lys Asp Glu Lys
1               5                   10                  15

Val Leu Tyr Leu
            20


<210> SEQ ID NO 15
<211> LENGTH: 6
<212> TYPE: PRT
<213> ORGANISM: Mycobacterium tuberculosis

<400> SEQUENCE: 15

Ala Arg Ala Val Gly Ile
1               5


<210> SEQ ID NO 16
<211> LENGTH: 8
<212> TYPE: PRT
<213> ORGANISM: Mycobacterium tuberculosis

<400> SEQUENCE: 16

Thr Asp Arg Val Ser Val Gly Asn
1               5


<210> SEQ ID NO 17
<211> LENGTH: 22
<212> TYPE: PRT
<213> ORGANISM: Mycobacterium tuberculosis
<220> FEATURE:
<221> NAME/KEY: VARIANT
<222> LOCATION: (17)..(17)
<223> OTHER INFORMATION: X = any amino acid

<400> SEQUENCE: 17

Asn Ser Lys Ser Val Asn Ser Phe Gly Ala His Asp Thr Leu Lys Val
1               5                   10                  15

Xaa Glu Arg Lys Arg Gln
            20
```

UNMARKED RECOMBINANT INTRACELLULAR PATHOGEN IMMUNOGENIC COMPOSITIONS EXPRESSING HIGH LEVELS OF RECOMBINANT PROTEINS

STATEMENT REGARDING FEDERALLY SPONSORED RESEARCH

This invention was made with Government support under Grant Nos. AI031338 and AI068413 awarded by the National Institutes of Health. The Government has certain rights in this invention.

CROSS REFERENCE TO RELATED APPLICATIONS

This application is an application under section 371 of International Patent Application No. PCT/US2008/066653 filed Jun. 12, 2008 and which claims the benefit of priority under 35 USC 119(e) for U.S. provisional application Ser. No. 60/944,051 filed Jun. 14, 2007, the entire contents of both of which are incorporated by reference herein.

FIELD OF THE INVENTION

The present invention provides a recombinant immunogenic composition for prevention or treatment of diseases of intracellular pathogens in mammals. Specifically, the recombinant intracellular compositions express a high level of a recombinant protein and do not contain an antibiotic resistance marker.

BACKGROUND OF THE INVENTION

It has long been recognized that parasitic microorganisms possess the ability to infect animals thereby causing disease and often death. Pathogenic agents have been a leading cause of death throughout history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic organisms are evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus *Mycobacterium*, complete all or part of their lifecycle within the cells of the infected host organism rather than extracellularly. Around the world, intracellular bacteria are responsible for untold suffering and millions of deaths each year. Tuberculosis is the leading cause of death from a single disease agent worldwide, with 8 million new cases and 2 million deaths annually. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, legionellosis (legionnaires' disease), lymphogranuloma venereum, brucellosis, plague, tularemia, salmonellosis, endemic typhus, murine typhus, Rocky Mountain Spotted fever, Scrub typhus, malaria, and Acquired Immunodeficiency Syndrome.

Currently it is believed that approximately one-third of the world's population is infected by *Mycobacterium tuberculosis* resulting in millions of cases of pulmonary tuberculosis annually. More specifically, human pulmonary tuberculosis primarily caused by *M. tuberculosis* is a major cause of death in developing countries. *Mycobacterium tuberculosis* is capable of surviving inside macrophages and monocytes, and therefore may produce a chronic intracellular infection. *Mycobacterium tuberculosis* is relatively successful in evading the normal defenses of the host organism by concealing itself within the cells primarily responsible for the detection of foreign elements and subsequent activation of the immune system. Moreover, many of the front-line chemotherapeutic agents used to treat tuberculosis have relatively low activity against intracellular organisms as compared to extracellular forms. These same pathogenic characteristics have heretofore limited the effectiveness of immunotherapeutic agents or immunogenic compositions against tubercular infections.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of nearly any organ including, but not limited to, the bones, spleen, kidney, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic.

When *M. tuberculosis* is not controlled by the infected subject it often results in the extensive degradation of lung tissue. In susceptible individuals lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation (conversion of affected tissues into a soft cheesy substance).

While *M. tuberculosis* is a significant pathogen, other species of the genus *Mycobacterium* also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic species of the genus *Mycobacterium* is *M. leprae* that causes millions of cases of the ancient disease leprosy. Other species of this genus which cause disease in animals and man include *M. kansasii, M. avium intracellulare, M. fortuitum, M. marinum, M. chelonei*, and *M. scrofulaceum*. The pathogenic mycobacterial species frequently exhibit a high degree of homology in their respective DNA and corresponding protein sequences and some species, such as *M. tuberculosis* and *M. bovis*, are highly related.

Attempts to eradicate tuberculosis using immunogenic compositions was initiated in 1921 after Calmette and Guérin successfully attenuated a virulent strain of *M. bovis* at the Institut Pasteur in Lille, France. This attenuated *M. bovis* became known as the Bacille Calmette Guérin, or BCG for short. Nearly eighty years later, immunogenic compositions derived from BCG remain the only prophylactic therapy for tuberculosis currently in use. In fact, all BCG immunogenic compositions available today are derived from the original strain of *M. bovis* developed by Calmette and Guérin at the Institut Pasteur.

Recently, significant attention has been focused on using transformed BCG strains to produce immunogenic compositions that express various cell-associated antigens. For example, C. K. Stover, et al. have reported a Lyme Disease immunogenic composition using a recombinant BCG (rBCG) that expresses the membrane associated lipoprotein OspA of *Borrelia burgdorferi*. Similarly, the same author has also produced a rBCG immunogenic composition expressing a pneumococcal surface protein (PsPA) of *Streptococcus pneumoniae*. (Stover C K, Bansal G P, Langerman S, and Hanson M S. 1994. Protective immunity elicited by rBCG immunogenic compositions. In: Brown F. (ed): Recombinant Vectors in Immunogenic composition Development. Dev Biol Stand. Dasel, Karger, Vol. 82:163-170)

Other intracellular pathogen diseases cause significant human health consequences. Leprosy continues to afflict approximately 6 million people worldwide and there is no effective vaccine to prevent it. A vaccine to prevent or treat leprosy would potentially have widespread use in endemic areas such as India and Brazil.

Therefore, more potent vaccine immunogenic compositions are needed against tuberculosis, other mycobacterial diseases and other infectious diseases caused by intracellular pathogens. The present inventors have now produced improved immunogenic compositions that induce protective immune responses against intracellular pathogens and do not contain antibiotic resistance markers. Vaccines containing antibiotic resistance markers may not obtain regulatory approval.

SUMMARY OF THE INVENTION

Disclosed herein are immunogenic compositions, and methods for the manufacture and use, for the prevention and treatment of intracellular pathogen diseases in humans and animals. The recombinant immunogenic compositions express high levels of recombinant proteins in vectors that do not harbor an antibiotic resistance marker ("unmarked").

The present disclosure allows the construction of recombinant immunogenic compositions against mycobacterial diseases and other infectious diseases that do not contain an antibiotic resistance marker and yet express large amounts of selected antigen(s).

The immunogenic compositions are administered intradermally or by another route, e.g. subcutaneously, intranasally, inhaled, or even orally to a mammalian host. The immunogenic compositions subsequently protect the mammalian hosts against infection with *Mycobacterium tuberculosis, M. leprae, M. avium*, other mycobacteria, and other intracellular pathogens.

Previously developed recombinant BCG immunogenic compositions have contained antibiotic resistance markers. These immunogenic compositions are suboptimal because they allow for the potential dissemination of antibiotic resistance markers. The present invention provides an unmarked recombinant BCG immunogenic composition. Furthermore, the immunogenic compositions allow exceptionally high expression of the selected antigen by using a shortened form of a potent promoter.

The technology described herein is applicable to other immunogenic compositions against intracellular pathogens such as *Francisella tularensis, Chlamydia* species, *Listeria monocytogenes, Brucella* species, *Yersinia pestis, Salmonella typhi, Leishmania* species, *Trypanosoma cruzi, Toxoplasma gondii, Histoplasma capsulatum, Riskettsia* species, *Coxiella burnetii, Plasmodia* species that cause malaria, and Human Immunodeficiency Virus (HIV).

In one embodiment, disclosed is an immunogenic composition comprising a recombinant attenuated intracellular pathogen wherein the recombinant attenuated intracellular pathogen expresses at least one major extracellular protein of an intracellular pathogen wherein a nucleic acid sequence encoding for the at least one major extracellular protein is incorporated into the intracellular pathogen's chromosome(s) under a strong promoter such that the major extracellular protein is over-expressed and the resulting recombinant intracellular pathogen does not harbor an antibiotic resistance marker.

In another embodiment, a method of constructing a recombinant attenuated intracellular pathogen vaccine expressing at least one antigenic protein of an intracellular pathogen wherein a nucleic acid sequence encoding for said at least one antigenic protein is incorporated into the intracellular pathogen's chromosome(s) under a strong promoter such that the antigenic protein is over-expressed and the resulting recombinant intracellular pathogen vaccine does not harbor an antibiotic resistance marker is provided, the method comprising the following steps: a) knocking out of an essential gene of a recombinant attenuated intracellular pathogen by homologous recombination using a selectable marker; b) constructing a gene cassette comprising a nucleic acid sequence encoding for the at least one antigen protein and a strong promoter adjacent to a cloned copy of a wild-type essential gene in a suitable vector for allelic exchange; and c) inserting the gene cassette into the chromosome of the recombinant attenuated intracellular pathogen adjacent to an essential gene such that the essential gene is restored by the cloned copy, the selectable marker is removed, and the antigenic protein is expressed.

In a further embodiment, an immunogenic composition is provided comprising a recombinant attenuated intracellular pathogen comprising an extrachromosomal nucleic acid sequence comprising at least one gene encoding for a major extracellular protein of an intracellular pathogen, the gene operably linked to a strong promoter and wherein the major extracellular protein is over-expressed and neither of the extrachromosomal nucleic acid sequence nor the recombinant attenuated intracellular pathogen harbor an antibiotic resistance marker.

In one embodiment, the recombinant attenuated intracellular pathogen is of the same species as the intracellular pathogen from which the major extracellular protein is derived. In another embodiment, the recombinant attenuated intracellular pathogen is of a different species than the intracellular pathogen from which the major extracellular protein is derived.

In another embodiment, the recombinant attenuated intracellular pathogen is selected from the group consisting of *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella burnetii, Leishmania* sp, *Toxpolasma gondii, Trypanosoma cruzi, Chlamydia pneumoniae, Chlamydia* sp, *Listeria monocytogenes, Listeria* sp, *Histoplasma* sp., *Francisella tularensis, Brucella* species, *Yersinia pestis, Bacillus anthracis*, and *Salmonella typhi.*

In yet another embodiment, the at least one major extracellular protein is from an intracellular pathogen selected from the group consisting of *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila* geno group, *Ehrlichia* sp., *Coxiella burnetii, Leishmania* sp., *Toxpolasma gondii, Trypanosoma cruzi, Chlamydia pneumoniae, Chlamydia* s.p, *Listeria monocytogenes, Listeria* sp., *Histoplasma* sp., *Francisella tularensis, Brucella species, Yersinia pestis, Bacillus anthracis*, and *Salmonella typhi.*

In other embodiments, the major extracellular proteins are non-fusion proteins. In another embodiment, the major extracellular proteins are fusion proteins under the control of a strong promoter.

In yet other embodiments, the recombinant attenuated intracellular pathogen is growth regulatable and selected from the group consisting of auxotrophs and metabolically impaired mutants. In still another embodiment, the metabolically impaired mutant is a siderophore mutant. In yet another embodiment, the growth regulatable recombinant attenuated intracellular pathogen is an auxotroph and wherein pantothenic acid is used to regulate growth of said auxotroph.

In another embodiment, the recombinant attenuated intracellular pathogen is a recombinant BCG.

In another embodiment, the major extracellular protein is a *M. tuberculosis* major extracellular protein. In another embodiment, the Mycobacteria major extracellular protein selected from the group consisting of the 12 kDa protein, 14 kDa protein, 16 kDa protein, 23.5 kDa protein, 24 kDa protein, 30 kDa protein, 32A kDa protein, 32B kDa protein, 45 kDa protein, 58 kDa protein, 71 kDa protein, 80 kDa protein, and 110 KD protein. In one embodiment, the major extracellular protein is the 30 kDa protein.

In another embodiment, the immunogenic composition further expresses at least one cytokine selected from the group consisting of interferon gamma, interleukin-2, interleukin-12, interleukin-4 receptor and granulocyte macrophage colony stimulating factor, and combinations thereof.

In one embodiment, the site of insertion is adjacent to an essential gene which can be deleted and subsequently restored under in vitro growth conditions. In another embodiment, the site of insertion is adjacent to a gene that encodes a protein that synthesizes a required nutrient. In another embodiment, the site of insertion is adjacent to the glnA1 gene. In another embodiment, the site of insertion is adjacent to a gene encoding a protein that synthesizes an essential molecule or an intermediate in the synthesis of an essential molecule. In yet another embodiment, the site of insertion is adjacent to a gene encoding a protein required for the acquisition of a required nutrient. In another embodiment, the site of insertion is adjacent to a gene encoding a protein required for iron acquisition. In another embodiment, the site of insertion is adjacent to mbtB.

In yet another embodiment, the promoter is the promoter for the *M. tuberculosis* rrs gene or a shortened derivative thereof.

In one embodiment, an immunogenic composition is provided comprising a recombinant attenuated intracellular pathogen, the recombinant attenuated intracellular pathogen expressing at least one antigenic protein wherein a nucleic acid sequence encoding for the at least one antigenic protein is incorporated into the intracellular pathogen's chromosome(s) under a strong promoter such that the at least one antigenic protein is over-expressed and the resulting recombinant intracellular pathogen does not harbor an antibiotic resistance marker. In another embodiment, the antigenic protein is selected from the group consisting of viral proteins, bacterial proteins, parasite-associated proteins and cancer-associated proteins.

DEFINITION OF TERMS

Figure 1A:
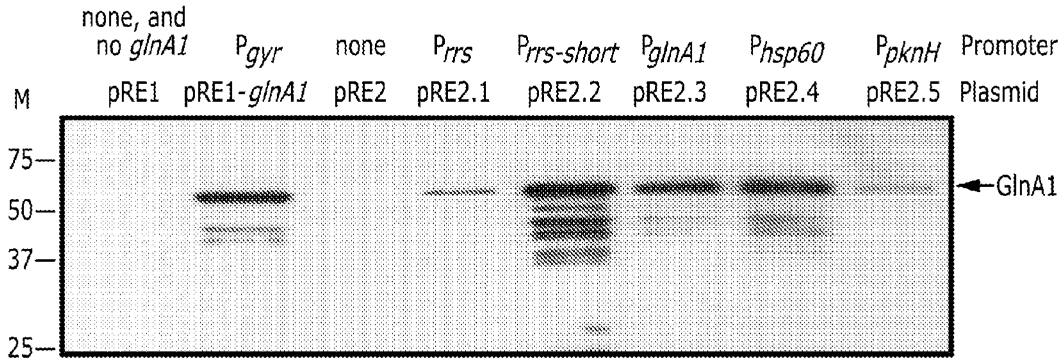
FIG. 1 depicts expression of *M. tuberculosis* GlnA1 (glutamine synthetase) by (A) recombinant *M. smegmatis* glnA1 strains and (B) recombinant BCG glnA1 strains, where expression is controlled by various promoters; and (C) expression and secretion of the *M. tuberculosis* 30 kDa major secretory protein by a recombinant BCG strain containing plasmid pRE4.2 ($P_{rrs\text{-}short}$ promoter).

To facilitate an understanding of the following Detailed Description, Examples and appended claims it may be useful to refer to the following definitions. These definitions are non-limiting in nature and are supplied merely as a convenience to the reader.

Auxotroph or auxotrophic: As used herein "auxotroph" refers to a microorganism having a specific nutritional requirement not required by the wild-type organism. In the absence of the required nutrient the auxotroph will not grow whereas the wild-type will thrive.

Gene: A "gene" as used herein refers to at least a portion of a genetic construct having a promoter and/or other regulatory sequences required for, or that modify the expression of, the genetic construct.

Genetic Construct: A "genetic construct" as used herein shall mean a nucleic acid sequence encoding for at least one major extracellular protein from at least one intracellular pathogen.

Growth Regulatable: As used herein the term "growth regulatable" refers to an auxotrophic or metabolically impaired form of the present invention's immunogenic compositions. In the case of auxotrophs, growth is regulated by providing a nutrient essential for the auxotroph's growth at a concentration sufficient to induce growth. In the case of the metabolically impaired siderophore-dependent rBCG, growth is regulated by supplying iron and a siderophore in vitro thereby preloading the rBCG with iron. The amount of subsequent growth in vivo is dependent upon the amount of iron-loading that took place during in vitro growth, which in turn is dependent upon the amount of iron and siderophore provided during in vitro growth.

Host: As used herein "host" refers to the recipient of the present immunogenic compositions. Exemplary hosts are mammals including, but not limited to, primates, rodents, cows, horses, dogs, cats, sheep, goats, pigs and elephants. In one embodiment of the present invention the host is a human. For the purposes of this disclosure host is synonymous with "vaccinee."

Immunogen: As used herein the term "immunogen" shall mean any substrate that elicits an immune response in a host. Immunogens of the present invention include, but are not limited to major extracellular proteins, and their recombinant forms, derived from intracellular pathogens, such as, but not limited members of the genus *Mycobacterium.*

Immunogenic Composition: An "immunogenic composition" as used herein comprises a recombinant vector, with or without an adjuvant, such as an intracellular pathogen, that expresses and/or secretes an immunogen in vivo and wherein the immunogen elicits an immune response in the host. The immunogenic compositions disclosed herein may be prototrophic, auxotrophic or metabolically impaired transformants. The immunogenic compositions of the present invention may or may not be immunoprotective or therapeutic. When the immunogenic compositions of the present invention prevent, ameliorate, palliate or eliminate disease from the host then the immunogenic composition may optionally be referred to as a vaccine. However, the term immunogenic composition is not intended to be limited to vaccines.

Major extracellular protein: As used herein, the term "major extracellular protein" is synonymous with "major secretory protein." Such proteins include proteins that are secreted using a classical secretion system as well as those released from the organism into its extracellular milieu by nonclassical or even unknown means. The present inventors have previously described and characterized the mycobacterial major extracellular proteins of the present invention. The descriptions and characterization of the present major extracellular proteins can be found, without limitation, in U.S. Pat. No. 6,599,510, issued Jul. 29, 2003, the entire contents of which are hereby incorporated by reference.

Extended N-terminal amino acid sequences of majorly abundant extracellular products were determined to provide primary structural data and to uncover possible relationships between the proteins. Sequencing was performed on the extracellular products using techniques well known in the art. Varying lengths of the N-terminal amino acid sequence, determined for each individual extracellular product, are shown below identified by the apparent molecular weight of the intact protein, and represented using standard one letter abbreviations for the naturally occurring amino acids. In keeping with established rules of notation, the N-terminal sequences are written left to right in the direction of the amino terminus to the carboxy terminus. Those positions where the identity of the determined amino acid is less than certain are underlined. Where the amino acid at a particular position is unknown or ambiguous, the position in the sequence is represented by a dash. Finally, where two amino acids are separated by a slash, the correct constituent has not been explicitly identified and either one may occupy the position in that sequence.

| PROTEIN | N-TERMINAL AMINO ACID SEQUENCE | SEQ ID NO. |
|---|---|---|
| 12 kDa | FDTRL MRLED EMKEG RYEVR AELPG VDPDK DVDIM VRDGQ LTIKA ERT | 1 |
| 14 kDa | ADPRL QFTAT TLSGA PFDGA S/NLQGK PAVLW | 2 and 3 |
| 16 kDa | AYPIT GKLGS ELTMT DTVGQ VVLGW KVSDL F/YKSTA VIPGY TV-EQ QI | 4 and 5 |
| 23 kDa | AETYL PDLDW DYGAL EPHIS GQ | 6 |
| 23.5 kDa | APKTY -EELK GTD | 7 |
| 24 kDa | APYEN LMVPS PSMGR DIPVA FLAGG PHAVY LLDAF NAGPD VSNWV TAGNA MMTLA -KGIC/S | 8 and 9 |
| 30 kDa | FSRPG LPVEY LQVPS PSMGR DIKVQ FQSGG NNSPA VYLLD | 10 |
| 32A kDa | FSRPG LPVEY LQVPS PSMGR DIKVQ FQSGG ANSP- LYLLD | 11 |
| 32B kDa | FSRPG LPVEY LQVPS A-MGR DI | 12 |
| 45 kDa | DPEPA PPVPD DAASP PDDAA APPAP ADPP- | 13 |
| 58 kDa | TEKTP DDVFK LAKDE KVLYL | 14 |
| 71 kDa | ARAVG I | 15 |

-continued

| PROTEIN | N-TERMINAL AMINO ACID SEQUENCE | SEQ ID NO. |
|---|---|---|
| 80 kDa | TDRVS VGN | 16 |
| 110 kDa | NSKSV NSFGA HDTLK V-ERK RQ | 17 |

Nucleic Acid Sequence: As used herein, the term "nucleic acid sequence" shall mean any continuous sequence of nucleic acids.

Over-expressed: As used herein, the term "over-expressed" shall mean expression of a recombinant antigenic protein by a recombinant intracellular pathogen such that the recombinant antigenic protein is expressed at a higher level than any corresponding endogenous protein. The recombinant antigenic protein can be from an intracellular pathogen Prototrophic: As used herein "prototrophic" refers to a rBCG that does not require any substance in its nutrition additional to those required by the wild-type.

Transformant: As used herein a "transformant" refers to a microorganism that has been transformed with at least one heterologous or homologous nucleic acid encoding for a polypeptide that is expressed and/or secreted. In one embodiment of the present invention the transformant is BCG.

DETAILED DESCRIPTION OF THE INVENTION

Unmarked strains of live vaccine vectors have been produced previously by various means. The most common method has relied on expression of the desired antigen from a plasmid using a balanced-lethal plasmid stabilization system that allows antibiotic resistance markers to be eliminated from the plasmid. Plasmid expression systems are often used to obtain high expression levels, as expression of genes integrated into the chromosome is frequently low level. However, genes integrated into the chromosome of live vaccine vectors are regarded as more stable than plasmid based genes. In contrast to the technology cited above, the present invention provides methodology for obtaining an unmarked strain and allows high expression from a gene integrated into the chromosome. Thus, the present disclosure provides both the stability advantage of chromosomal integration and the advantage of high expression of a recombinant antigen.

Newer, site-specific integration methods for incorporating genes into the chromosome without antibiotic resistance genes have been developed, but these methods have been developed using *Escherichia coli* and may not work in unrelated bacteria without a great deal of engineering. Furthermore, these methods are limited to a single site of integration on the chromosome. Although in the present disclosure the integration is located at a single site (in the glnA1 locus), the method could be used to integrate genes in many locations on the chromosome, wherever an essential gene can be deleted and subsequently restored. Multiple integrations could also be done sequentially with this method, incorporating multiple genes at different locations on the chromosome.

In previous studies, genes have been incorporated into the his locus of *Salmonella* via homologous recombination (without antibiotic resistance genes) for the purpose of expression in a live vaccine vector. In one study, expression from the chromosome was shown to be far more stable than expression from a plasmid, but expression was also greatly reduced, thus weakening the immune response to the vaccine. In contrast, the present disclosure combines the stability of chromosomal integration with high expression of a recombinant antigen. Furthermore, the present methods and compositions utilize substitution via homologous recombination into the glnA1 locus, allowing selection based on a requirement for glutamine for growth. Finally, substitution via homologous recombination into the glnA1 locus with the use of a specific promoter allows high expression.

Recombinant BCG Expressing and Secreting Major Extracellular Proteins

Figure 1B:
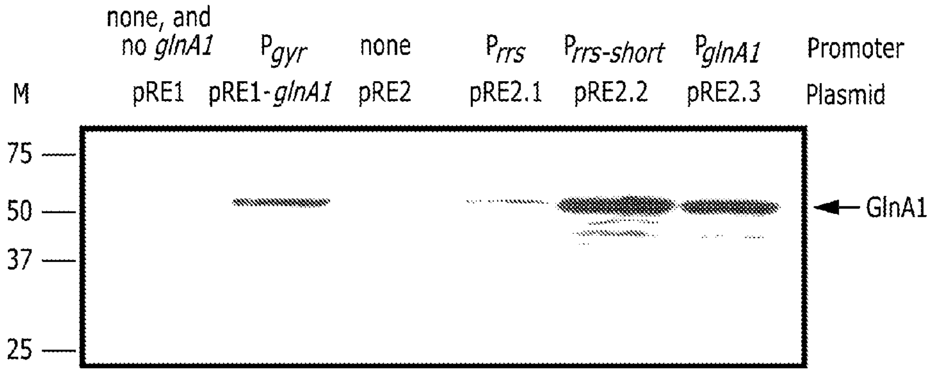
Figure 1C:
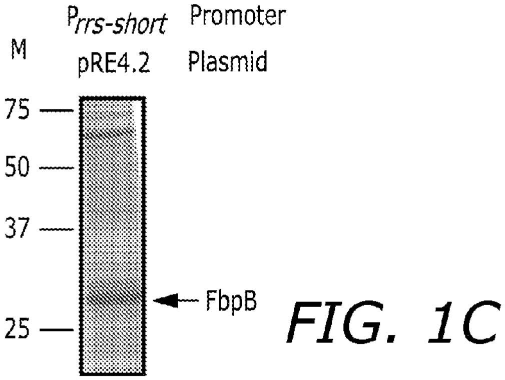

Selection of a Strong Promoter:

As overexpression of the *M. tuberculosis* 30 kDa major secretory protein from the chromosome would likely require a very strong promoter, the relative strength of several reportedly strong promoters was assessed using a plasmid system. The plasmid pRE1 was first constructed from pNBV1 (Howard et al., Gene 166:181-182, 1995) and a synthetic sequence generated by PCR assembly, which contained several strong transcriptional terminators ($T_{tonB}$, $T_{fd}$, rrnB$T_1T_2$, T7Te, and $T_{tetA}$) to allow for the isolation of one or more transcriptional units. The *M. tuberculosis* glnA1 gene was cloned into pRE1 without a promoter or under the control of various promoters, and the resulting plasmids transformed by electroporation into an *M. smegmatis* glnA1 mutant (glutamine auxotroph). The promoters selected for these studies were: $P_{gyr}$, the promoter for the *Mycobacterium smegmatis* DNA gyrase genes; $P_{rrs}$, the promoter for the *M. tuberculosis* rrs gene (also known as rrnS, MTB000019 and the 16S ribosomal RNA gene); $P_{rrs\text{-}short}$, a shortened derivative of $P_{rrs}$ lacking the boxA, boxB, and boxC elements; $P_{glnA1}$, the promoter for the *M. tuberculosis* glnA1 gene, the glutamine synthetase GlnA1 protein gene; $P_{hsp60}$, the promoter for the *M. tuberculosis* heat shock protein 60 gene also known as groEL2; and $P_{pknH}$, the promoter for the *M. tuberculosis* pknH gene, also known as Rv1266c. The plasmid containing the glnA1 gene without a promoter did not complement the glnA1 mutant, indicating that background expression of glnA1 (due to read-through transcription from other promoters on the plasmid) was tightly controlled. All of the plasmids containing the glnA1 gene with a promoter were capable of complementing the glnA1 mutant. Cell lysates (from equal volumes of culture) of the *M. smegmatis* glnA1 recombinant strains were analyzed by polyacrylamide gel electrophoresis and immunoblotting with polyvalent, highly specific rabbit anti-GlnA1 immunoglobulin (FIG. 1A). Surprisingly, expression from the full length rrs promoter (pRE2.1) and the pknH promoter (pRE2.5) was relatively weak, in contrast to previous reports on these promoters (Agarwal and Tyagi, FEMS Microbiol Lett 225:75-83, 2003; Verma et al., Gene 148:113-118, 1994). Expression from the $P_{glnA1}$ and $P_{hsp60}$ promoters (pRE2.3 and pRE2.4, respectively) was high, as we have previously observed for these promoters in other contexts (Tullius et al. Infect Immun 69:6348-6363, 2001), however, the highest expression out of all the promoters was obtained with a shortened derivative of the rrs promoter ($P_{rrs\text{-}short}$, plasmid pRE2.2) that was engineered to remove the boxA, boxB, and boxC sequences and incorporate a Shine-Dalgarno (SD) sequence matched to the *M. tuberulosis* 16S rRNA anti-SD sequence. Similar results were obtained when the same plasmids were used to transform a BCG glnA1 mutant (FIG. 1B). The *M. tuberculosis* glnA1 gene in pRE2.2 was replaced with the *M. tuberculosis* 30 kDa major secretory protein gene (fbpB) to generate plasmid pRE4.2. This plasmid was transformed into BCG by electroporation, and expression of the *M. tuberculosis* 30 kDa major secretory protein (FbpB) from the $P_{rrs\text{-}short}$ promoter was very high, as observed for expression of GlnA1 from this promoter (FIG. 1C).

Figure 2:
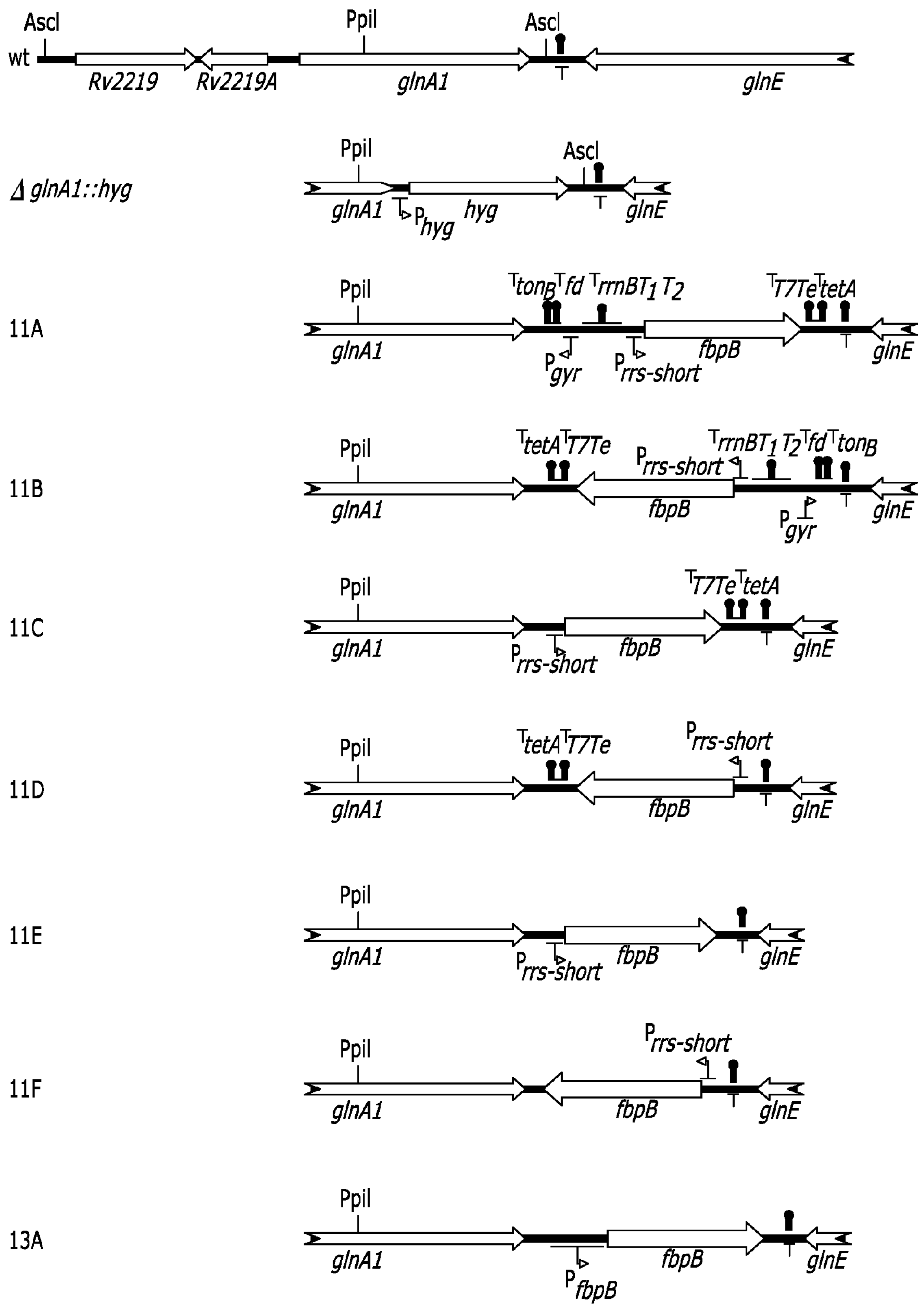
FIG. 2 depicts the allelic exchange substrates used in the construction of the fbpB integration strains.
Figure 3:
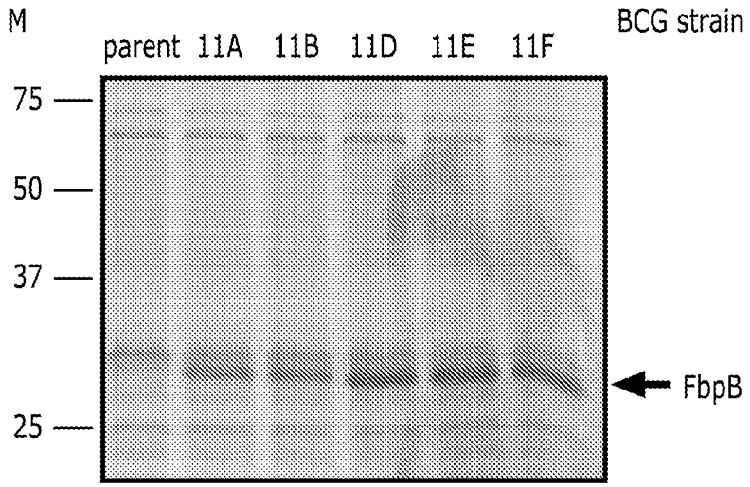
FIG. 3 depicts expression and secretion of the *M. tuberculosis* 30 kDa major secretory protein by the fbpB integration strains 11A, 11B, 11D, 11E, and 11F.
Figure 4:
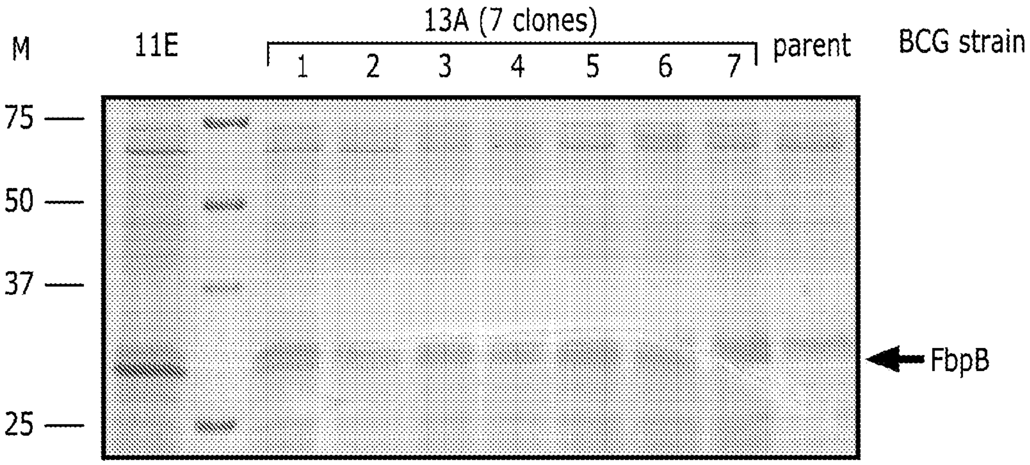
FIG. 4 depicts expression and secretion of the *M. tuberculosis* 30 kDa major secretory protein by the fbpB integration strains 13A and 11E.
Figure 5:
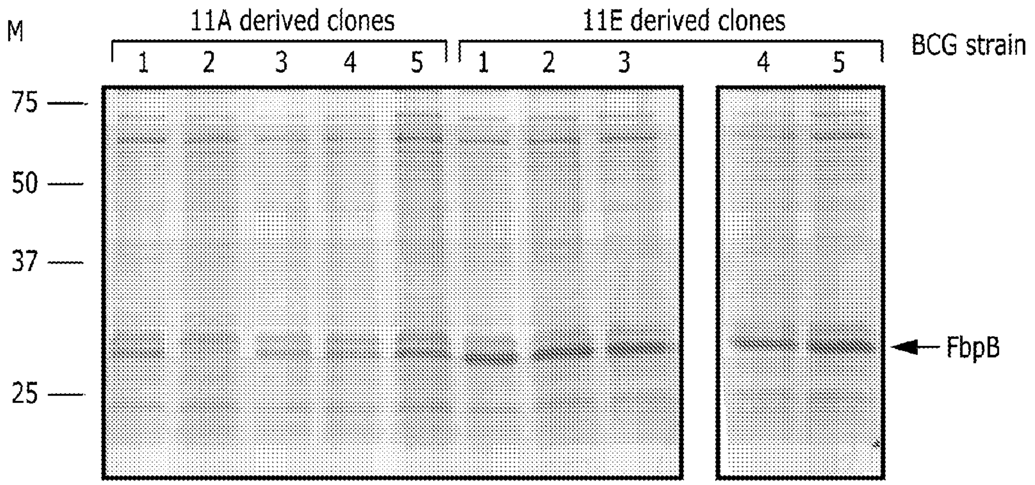
FIG. 5 depicts expression and secretion of the *M. tuberculosis* 30 kDa major secretory protein by unmarked, prototrophic clones derived from the fbpB integration strains 11A and 11E.
Figure 6:
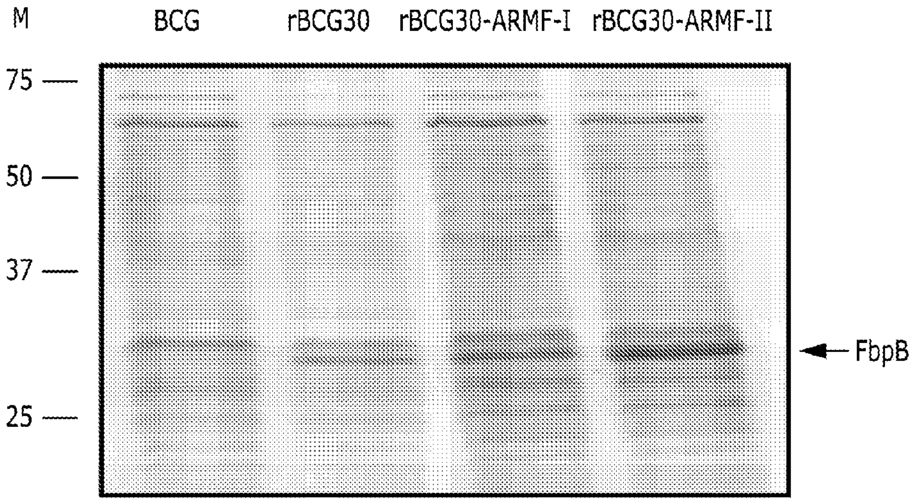
FIG. 6 depicts expression and secretion of the *M. tuberculosis* 30 kDa major secretory protein by the unmarked, prototrophic fbpB integration strains rBCG30-ARMF-I and rBCG30-ARMF-II.

Unmarked Integration of an Expression Cassette by a Two Step Allelic Exchange Procedure:

Recombinant BCG strains that over-express and secrete the *M. tuberculosis* 30 kDa major secretory protein were constructed by a two-step procedure that resulted in the stable integration of the fbpB gene into the BCG chromosome without leaving an antibiotic resistance marker, or any other extraneous DNA, in the strains. In the first step, a BCG glnA1 mutant (glutamine auxotroph) was generated from the parental BCG strain, via allelic exchange, incorporating a hygromycin resistance gene into the chromosome. In the second step, the fbpB gene along with a strong promoter was integrated into the glnA1 locus, via allelic exchange, and at the same time the mutated glnA1 allele was replaced with the wild-type glnA1 allele. Thus, the glutamine auxotroph from the first step was converted back to a glutamine prototroph and the hygromycin resistance gene was removed from the strain. For the first step, the allelic exchange substrate was generated using a cloning strategy in which a glnA1 locus with a 852 bp deletion at the 3' end of the glnA1 coding region was created with a hygromycin resistance ($hyg^r$) gene inserted at the site of the deletion (FIG. 2; ΔglnA1::hyg). This mutated allele was cloned into the allelic exchange vector phEX2 [a derivative of phEX1, itself a derivative of phAE87 (Bardarov et al., Microbiology 148:3007-3017, 2002)] to generate phEX2 ΔglnA1::hyg. This plasmid was electroporated into *M. smegmatis* to generate specialized transducing phage. BCG strains were infected with this purified phage and clones that had undergone a homologous recombination event were selected based on their resistance to hygromycin and then screened for glutamine auxotrophy. The allelic exchange substrates for the second step were generated using a cloning strategy in which an fbpB cassette, containing the fbpB gene with a strong promoter upstream to drive expression was cloned into the AscI site of a wild-type glnA1 locus, just downstream of the glnA1 coding region (FIG. 2; 11A, 11B, 11C, 11D, 11E, 11F, and 13A). These mutated alleles were cloned into the allelic exchange vector phEX2 and specialized transducing phage was prepared in *M. smegmatis*, as above. BCG glutamine auxotrophs generated in the first step were infected with purified phage and clones that had undergone a homologous recombination event were selected based on their ability to grow in the absence of L-glutamine (i.e. a functional glnA1 allele was restored). Removal of the hygromycin gene was confirmed by culturing the strains on agar plates with and without hygromycin. Hygromycin sensitive, glutamine prototrophs were screened for expression and export of recombinant *M. tuberculosis* 30 kDa major secretory protein by polyacrylamide gel electrophoresis. This method was highly successful as 102 out of 111 clones that grew in the absence of L-glutamine were hygromycin sensitive (92%) and 24 out of 25 of the hygromycin sensitive clones overexpressed the 30 kDa major secretory protein (96%).

rBCG30-ARMF-I Tice and rBCG30-ARMF-II Tice:

The initial fbpB integration strains were constructed using rBCG(panCD) and rBCG(mbtB) as the parental strains. Although expression of FbpB from the $P_{rrs\text{-}short}$ promoter was very strong on the plasmid pRE4.2 (FIG. 1C), whether expression of FbpB would be affected once integrated into the chromosome or whether this expression might have a detrimental effect on the expression of the genes flanking the integration site, glnA1 and glnE, was unknown. Therefore, six different fbpB integration strains were constructed using the fbpB cassette from pRE4.2 that differed in the orientation of the fbpB gene and in the number of transcriptional terminators upstream and/or downstream of fbpB (FIG. 2; 11A, 11B, 11C, 11D, 11E, and 11F). Five of the six desired strains were constructed in the rBCG(panCD) parental strain (no clones were obtained for 11C) and the strains were analyzed for expression and export of recombinant *M. tuberculosis* 30 kDa major secretory protein by polyacrylamide gel electrophoresis (FIG. 3). All five strains overexpressed the 30 kDa major secretory protein, but the 11D, 11E, and 11F clones all expressed the protein at higher levels than the 11A and 11B clones. The 11A and 11B strains both contained three transcriptional terminators upstream of the $P_{rrs\text{-}short}$ promoter, while the other three strains lack these terminators. As orientation of fbpB in the 11D, 11E, and 11F strains did not affect expression, the lowered expression in the 11A and 11B strains is likely not due to blocking read-through transcription from upstream promoters, but due to down-regulating the strength of the $P_{rrs\text{-}short}$ promoter (most likely due to the proximity of the $rrnBT_1T_2$ terminator). For comparison, strain 13A, which is similar to 11E except that the endogenous fbpB promoter was used instead of the $P_{rrs\text{-}short}$ promoter, was constructed. Expression of the 30 kDa major secretory protein was weak compared with strain 11E (FIG. 4). Two strains were selected for further analysis; a moderate expressing strain (11A) and a high expressing strain (11E). Both strains stably expressed and exported the 30 kDa major secretory protein for at least 28 generations (4 subcultures, 1:100 dilutions). As these initial fbpB integration strains were constructed using rBCG (panCD) as the parental strain, the panCD locus needed to be restored to generate wild-type, prototrophic, fbpB integration strains that are completely free of antibiotic resistance markers. To accomplish this, an allelic exchange substrate encoding a wild-type panCD locus was cloned into the allelic exchange vector phEX2 and specialized transducing phage was prepared in *M. smegmatis*, as above. The 11A and 11E strains were infected with purified phage and clones that had undergone a homologous recombination event were selected based on their ability to grow in the absence of pantothenate (i.e. a functional panCD locus was restored). Removal of the apramycin gene that marked the panCD mutation was confirmed by culturing the strains on agar plates with and without apramycin. Five apramycin sensitive, pantothenate prototrophs, for both the 11A and 11E strains, were randomly selected and screened for expression and export of recombinant *M. tuberculosis* 30 kDa major secretory protein by polyacrylamide gel electrophoresis. All ten clones maintained a similar level of expression of the 30 kDa major secretory protein compared with their parental strains (11A and 11E), further evidence of the stability of the strains' expression levels (FIG. 5). A single clone derived from the 11A strain was selected and designated as rBCG30-ARMF-I. Likewise, a single clone derived from the 11E strain was selected and designated as rBCG30-ARMF-II. These two strains were compared to BCG and rBCG30 for expression and export of recombinant *M. tuberculosis* 30 kDa major secretory protein by polyacrylamide gel electrophoresis (FIG. 6). The rBCG30-ARMF-I strain was found to produce 9.5 fold more, and the rBCG30-ARMF-II strain was found to produce 15.5 fold more, of the 30 kDa antigen per mL of culture than the control BCG Tice strain. Surprisingly, this expression of the 30 kDa antigen from the chromosome was 1.6 fold and 2.6 fold more than that of rBCG30 where expression is from a multicopy plasmid.

Figure 7:
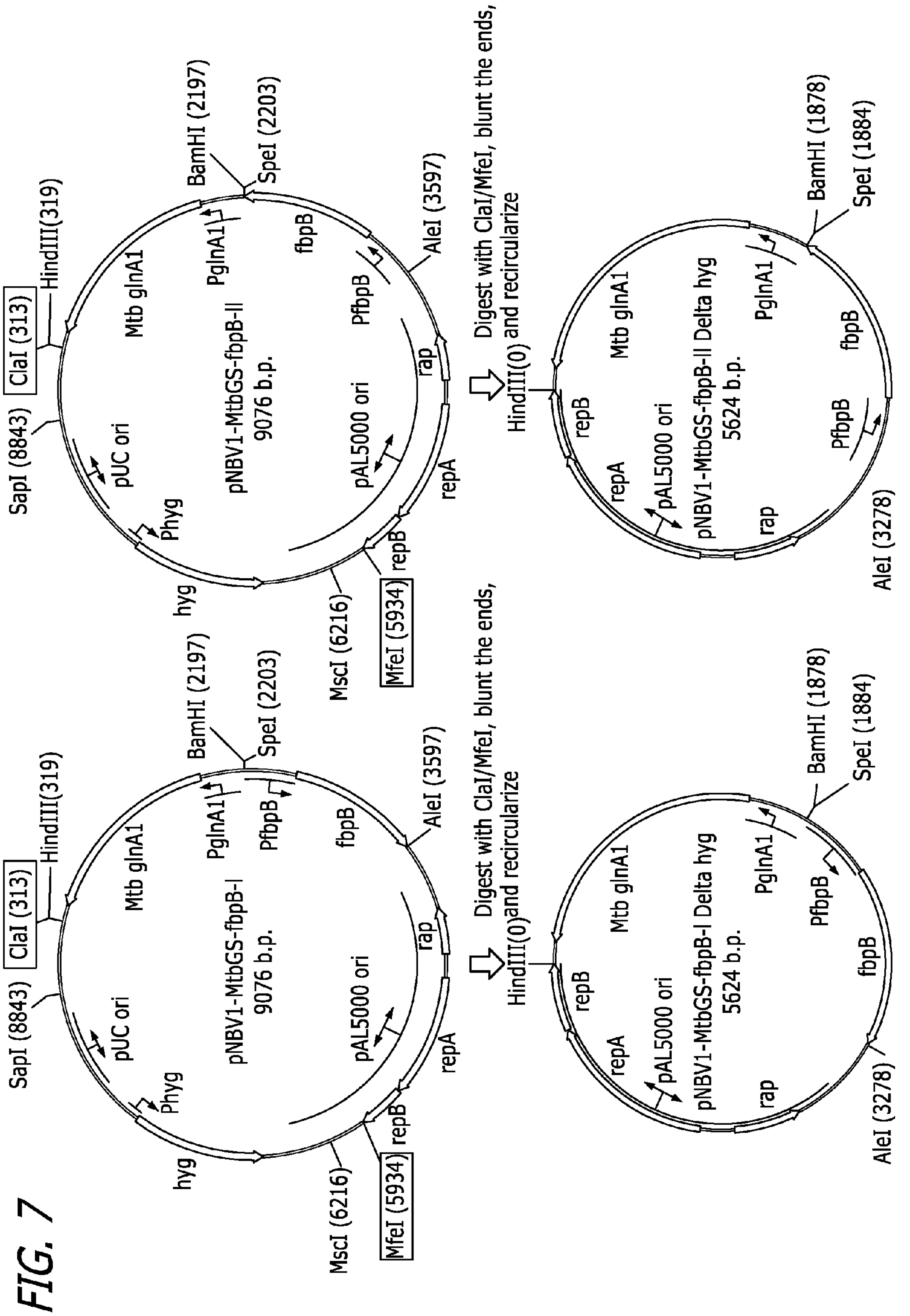
FIG. 7 depicts maps of the expression plasmids pNBV1-MtbGS-fbpB-I, pNBV1-MtbGS-fbpB-II, pNBV1-MtbGS-fbpB-I Δhyg, and pNBV1-MtbGS-fbpB-II Δhyg.

Construction of an antibiotic resistance marker free plasmid containing an expression cassette and glnA1 for balanced-lethal plasmid stabilization in mycobacterial glnA1 strains: The plasmid pNBV1-MtbGS, which was previously used to complement mycobacterial glnA1 mutants, was first modified to contain an fbpB expression cassette that consists of the fbpB coding region along with the endogenous fbpB promoter, generating plasmids pNBV1-MtbGS-fbpB-I and pNBV1-MtbGS-fbpB-II (FIG. 7). In plasmid pNBV1-MtbGS-fbpB-I the fbpB gene is in the opposite orientation of glnA1 and in plasmid pNBV1-MtbGS-fbpB-II the fbpB gene is in the same orientation as glnA1. The hygromycin resistance gene as well as the *E. coli* plasmid origin of replication were removed from these plasmids by digestion with ClaI and MfeI, blunting of the DNA termini, and self-ligation to recircularize the plasmids. The ligation products were electroporated into a *M. smegmatis* glnA1 mutant and clones were selected that grew in the absence of glutamine (i.e. the mutant was complemented by the plasmid) and were hygromycin sensitive. Total DNA was isolated and plasmid DNA was purified away from genomic DNA on low melting point agarose gels. The plasmid DNA was confirmed to be correct by restriction analysis and the plasmids were designated pNBV1-MtbGS-fbpB-I Δhyg and pNBV1-MtbGS-fbpB-II Δhyg (FIG. 7).

Figure 8:
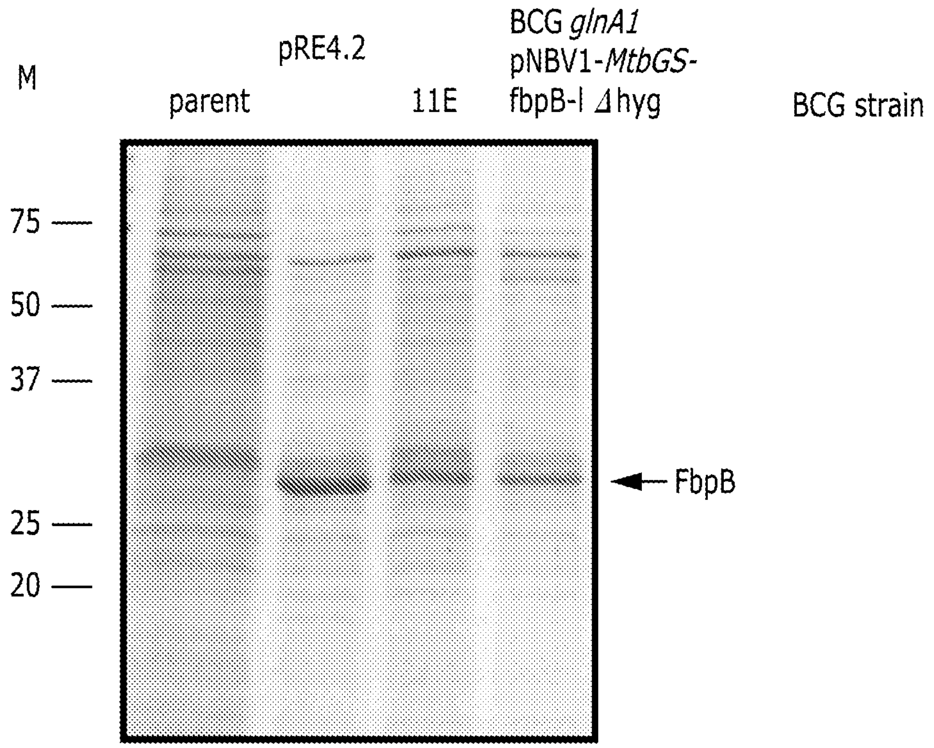
FIG. 8 depicts expression and secretion of the *M. tuberculosis* 30 kDa major secretory protein by the BCG glnA1 pNBV1-MtbGS-fbpB-I Δhyg strain containing the unmarked plasmid pNBV1-MtbGS-fbpB-I Δhyg.

BCG glnA1 pNBV1-MTBGS-fbpB-I Δhyg and BCG glnA1 pNBV1-MTBGS-fbpB-II Δhyg:

The two plasmids described above lacking the hygromycin resistance gene and the *E. coli* plasmid origin of replication (pNBV1-MtbGS-fbpB-I Δhyg and pNBV1-MtbGS-fbpB-II Δhyg) were electroporated into a BCG glnA1 mutant and four clones (for each plasmid) that grew in the absence of glutamine (i.e. the mutant was complemented by the plasmid) were selected for expression analysis. All eight clones appeared to be overexpressing the 30 kDa antigen. One clone of each strain was saved and designated BCG glnA1 pNBV1-MtbGS-fbpB-1 Δhyg and BCG glnA1 pNBV1-MtbGS-fbpB-II Δhyg. As the orientation of the fbpB expression cassette did not influence the expression level of the 30 kDa antigen, one strain (BCG glnA1 pNBV1-MtbGS-fbpB-I Δhyg) was selected for further analysis and was compared to BCG and other recombinant BCG strains overexpressing the 30 kDa antigen (FIG. 8). BCG glnA1 pNBV1-MtbGS-fbpB-I Δhyg had an expression profile similar to other recombinant BCG strains overexpressing the 30 kDa antigen and was found to produce 10.6 fold more of the 30 kDa antigen per mL of culture than the control BCG Tice strain. In this particular example, the BCG glnA1 mutant used to create the BCG glnA1 pNBV1-MTBGS-fbpB-I Δhyg strain contains an antibiotic resistance marker in the chromosome (a kanamycin resistance gene inserted in the glnA1 gene). The unmarked plasmids, pNBV1-MtbGS-fbpB-I Δhyg and pNBV1-MtbGS-fbpB-II Δhyg, can be used in exactly the same way with an unmarked BCG glnA1 strain to generate a vaccine strain that contains no antibiotic resistance markers.

In one embodiment, immunogenic compositions are provided comprising a rBCG wherein the rBCG is metabolically impaired and wherein a siderophore and iron are used to regulate growth of the metabolically impaired strain. This rBCG has been rendered siderophore-dependent and iron-loadable. It can be grown in vitro in the presence of iron and a siderophore such as, but not limited to, mycobactin J or exochelin, and thereby loaded with iron. Subsequently, when administered to the host, it can use the stored iron to multiply for several generations. As some growth of a live vaccine in the host is necessary to induce a strong protective immune response, the capacity of the rBCG to divide several times in the host allows the generation of a strong protective immune response. At the same time, the limited capacity of the rBCG to multiply in the host, as a result of its inability to acquire iron in the host, renders it unable to cause disseminated disease in the immunocompromised host and therefore safer than BCG.

In another embodiment, growth regulatable recombinant BCG immunogenic compositions, which can not grow more than a few generations in the host without a nutritional supplement, are designed to be safer than BCG, because unlike BCG, such immunogenic composition can not disseminate in the host in the absence of the nutritional supplement. Growth-regulatable recombinant BCG immunogenic compositions having antibiotic resistance markers are disclosed in co-pending International Patent Application PCT/US2007/066348, which is incorporated by reference herein for all it contains regarding growth regulatable recombinant BCG. Growth-regulatable auxotrophic recombinant BCG immunogenic compositions are provided that are dependent upon small amounts of the vitamin pantothenate. The rBCG can be administered to the host without providing a nutrient supplement to the host, in which case it can only undergo a limited number of divisions using stored nutrient but a sufficient number of divisions to generate a potent protective immune response. Alternatively, the vaccine can be administered to the host and the host provided a large amount of the nutrient, which can be given safely and inexpensively to mammals in large quantities, facilitating its acquisition by the live recombinant immunogenic composition in the host. In a non-limiting embodiment, the nutrient is the vitamin pantothenate. Under such circumstances, the immunogenic composition can persist longer in the host and induce a stronger protective immune response. Should the vaccine begin to disseminate and cause illness the nutrient supplement can be readily terminated, thereby stopping growth of the organism in the host and preventing serious disease. The amount of pantothenate normally present in the host eating a normal diet is orders of magnitude less than that needed to provide sufficient pantothenate for the growth of the rBCG. One embodiment of the live recombinant pantothenate-dependent BCG immunogenic composition over-expresses the *M. tuberculosis* 30 kDa major secretory protein.

Embodiments therefore provide recombinant strains of BCG that are growth-limited and/or growth-regulatable including strains that secrete pathogen major extracellular proteins including *M. tuberculosis* major extracellular proteins.

The immunogenic compositions are administered intradermally or by another route, e.g. subcutaneously, intranasally, inhaled, or even orally to a mammalian host. The immunogenic compositions are suitable for both immunocompetent and immunocompromised hosts. The immunogenic compositions induce a strong cell-mediated immune response to pathogen antigens in the vaccine. The immunogenic compositions subsequently protect the mammalian hosts against infection with *M. tuberculosis, Mycobacterium leprae, Mycobacterium avium*, other Mycobacteria, and other intracellular pathogens.

Additionally, the current commercially available BCG vaccine against tuberculosis is of limited efficacy against pulmonary tuberculosis. The immunogenic compositions disclosed herein are more potent than the current commercially available vaccine in protecting against pulmonary tuberculosis and dissemination of bacteria to the spleen and other organs. Additionally, the immunogenic compositions are safer than the current commercially available vaccine in that the immunogenic compositions are unable to disseminate in the immunocompromised host.

Despite the stability advantages of chromosome integration, expression of a recombinant antigen from a plasmid may produce a strain with a different phenotype than a strain expressing a recombinant antigen from the chromosome and therefore may potentially produce a superior immune response. Therefore, the present disclosure allows for the expression of the desired antigen from a plasmid using balanced-lethal plasmid stabilization. The plasmid lacks antibiotic resistance markers and contains glnA1, which allows the plasmid to be stably maintained in mycobacterial glnA1 mutants.

Previously, it was known that the immunostimulatory cytokines interleukin 2 (IL-2), interleukin 12 (IL-12), granulocyte-macrophage colony stimulating factor (GM-CSF) and interferon gamma (INFγ) are associated with enhanced cell-mediated immunity against intracellular pathogens including *Mycobacterium tuberculosis*. For example, IL-12 enhances the resistance of mice to *M. tuberculosis* and mice lacking INFγ show increased susceptibility to *M. tuberculosis*. These immunostimulatory cytokines, when present in close proximity to the *M. tuberculosis* 30 kDa major secretory protein or other *M. tuberculosis* major extracellular proteins can enhance the protective immune response against tuberculosis induced by the extracellular proteins. Moreover, a recombinant BCG immunogenic composition co-expressing one of these immunostimulatory cytokines and the 30 kDa major secretory protein or other *M. tuberculosis* major extracellular proteins induces greater protective immunity than a recombinant BCG vaccine expressing the extracellular protein in the absence of the immunostimulatory protein. Recombinant BCG immunogenic compositions expressing immunostimulatory proteins and having antibiotic resistance markers are disclosed in co-pending International Patent Application PCT/US2007/066350 which is incorporated by reference herein for all it contains regarding immunostimulatory recombinant BCG.

Previous studies have shown that immunostimulatory cytokines, e.g. IL-2 and IL-12, can augment the efficiency of subunit vaccines. However, none of the previously reported subunit vaccines have approached the efficacy of BCG. Furthermore, previously disclosed cytokine-producing recombinant BCG vaccines did not induce more potent protection in animal models than rBCG alone. The present inventors have determined that a recombinant BCG vaccine expressing only INFγ was not more potent than the parent BCG strain. Surprisingly, the recombinant BCG co-expressing INFγ and the 30 kDa *M. tuberculosis* major secretory protein was more potent than rBCG30, the strain only expressing the 30 kDa protein. Thus, when expressed by BCG, INFγ did not enhance the level of protective immunity conferred by BCG alone, but when expressed by rBCG30, it did enhance the level of protective immunity conferred by rBCG30 alone. Therefore, the present inventors have determined that the co-expression of a majorly abundant extracellular antigen from an intracellular pathogen and a cytokine will result in enhanced protective immunity.

The present disclosure provides recombinant BCG immunogenic compositions expressing cytokines including, but not limited to, interleukin-2 (IL-2), interleukin-10 (IL-10), interleukin-12 (IL-12), interleukin-4 (IL-4), interleukin-6 (IL-6), interleukin-7 (IL-7), interleukin-8 (IL-8), interleukin-15 (IL-15), interleukin-18 (IL-18), interferon gamma, tumor necrosis factor alpha (TNF-alpha), granulocyte macrophage colony stimulating factor (GM-CSF). The human cytokines IL-2, IL-12, and GM-CSF have been reported to be active in the guinea pig and active in non-glycosylated form. Additionally, rBCGs expressing cytokine receptors such as, but not limited to, the soluble IL-4 receptor (sIL4R) and the receptors for IL-2, IL-4, IL-7, IL-12, IFNs, GM-CSF or TNF-alpha are disclosed.

Cell-Mediated, Humoral, and Protective Immunity Studies

The studies of the efficacy of the vaccines utilized guinea pigs because the guinea pig model is especially relevant to human tuberculosis clinically, immunologically, and pathologically. In contrast to the mouse and rat, but like the human, the guinea pig a) is susceptible to low doses of aerosolized *M. tuberculosis*; b) exhibits strong cutaneous delayed-type hypersensitivity (DTH) to tuberculin; and c) displays Langhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of vaccine efficacy.

EXAMPLES

Example 1

Production of Bacteria Inocula

Aliquots were removed from logarithmically growing wild-type or recombinant BCG cultures, and the bacteria were pelleted by centrifugation at 3,500×g for 15 min. The bacteria are then washed with 1× phosphate buffered saline (1×PBS, 50 mM sodium phosphate pH 7, 150 mM sodium chloride) and resuspended at a final concentration of $1\times10^4$ or $1\times10^7$ colony-forming units per ml in 1×PBS. The immunization inoculum contains $10^3$ or $10^6$ viable wild-type or recombinant BCG bacteria in a total volume of 100 μl.

Example 2

Immunization of Animals

Specific-pathogen free 250-300 g outbred male Hartley strain guinea pigs from Charles River Breeding Laboratories, in groups of 15 or 21, were sham-immunized by intradermal administration of buffer (15 animals total) or immunized intradermally with $10^3$ CFU of one of the following strains of recombinant BCG (21 animals/group):

Group A: Sham-immunized (Sham)
Group B: BCG Tice Parental Control (BCG)
Group C: rBCG30 Tice I (pSMT3-MTB30) (rBCG30)
Group J: rBCG30-ARMF-I
Group K: rBCG30-ARMF-II

Example 3

Cutaneous Delayed-Type Hypersensitivity (DTH) to Purified Recombinant *M. tuberculosis* 30 kDa Major Secretory Protein (r30)

Ten weeks after immunization, 6 guinea pigs in each group were shaved over the back and injected intradermally with 10 μg of purified recombinant *M. tuberculosis* 30 kDa major secretory protein (r30) in 100 μl phosphate buffered saline. After 24 h, the diameter of erythema and induration was measured. A separate group of animals from the one used in the challenge studies is used for skin-testing to eliminate the possibility that the skin test itself might influence the outcome. The results are summarized in Table 1.

TABLE 1

Cutaneous DTH - Experiment 1

| Group | Strain | Test Antigen | Erythema (mm ± SE) | Induration (mm ± SE) |
|---|---|---|---|---|
| A | Sham | r30 | 0 ± 0 | 0 ± 0 |
| B | BCG | r30 | 6 ± 2.2 | 0 ± 0 |
| C | rBCG30 | r30 | 16.8 ± 1.3 | 12.4 ± 3.9 |
| J | rBCG30-ARMF-I | r30 | 10.6 ± 2.3 | 2.6 ± 2.6 |
| K | rBCG30-ARMF-II | r30 | 15.1 ± 0.8 | 10.7 ± 3.4 |

These results showed that sham-immunized animals (Group A) and animals immunized with the parental BCG Tice strain (Group B) had no induration upon testing with r30. Animals immunized with the unmarked strain rBCG30-ARMF-I (Group J), had little induration upon testing with r30. In contrast, animals immunized with the unmarked strain rBCG30-ARMF-II (Group K) had significant induration upon testing with r30, similar to animals immunized with rBCG30 (Group C).

Example 4

Protective Immunity to Aerosol Challenge

Ten weeks after immunization, the remaining animals were challenged with an aerosol generated from a 10 ml single-cell suspension containing $3\times10^4$ colony forming units (CFU) of *M. tuberculosis* per ml. Prior to challenge, the challenge strain, *M. tuberculosis* Erdman strain (ATCC 35801), was passaged through outbred guinea pigs to maintain virulence, cultured on 7H11 agar, subjected to gentle sonication to obtain a single cell suspension, and frozen at −70° C. This aerosol dose delivers approximately 10 live bacilli to the lungs of each animal. The airborne route of infection was used because this is the natural route of infection for pulmonary tuberculosis. A relatively large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 2.

TABLE 2

CFU in Lungs and Spleens - Experiment 1

| Group | Strain | Lung (Mean Log CFU ± SE) | Spleen (Mean Log CFU ± SE) |
|---|---|---|---|
| A | Sham | 7.73 ± 0.14 | 7.64 ± 0.25 |
| B | BCG | 4.68 ± 0.15 | 4.35 ± 0.08 |
| C | rBCG30 | 3.82 ± 0.12 | 3.19 ± 0.20 |
| J | rBCG30-ARMF-I | 4.53 ± 0.08 | 4.02 ± 0.13 |
| K | rBCG30-ARMF-II | 4.27 ± 0.13 | 3.72 ± 0.17 |

These results showed that animals immunized with BCG or any recombinant BCG strain had much lower CFU in the lungs and spleens than the sham-immunized animals.

Animals immunized with the unmarked strain rBCG30-ARMF-I (Group J) had fewer CFU in the lung (0.15 log) and spleen (0.32 log) than BCG (Group B), however the differences were not statistically significant. In contrast, animals immunized with the unmarked strain rBCG30-ARMF-II (Group K) had even fewer CFU in the lung (0.42 log, P=0.01 by ANOVA) and spleen (0.63 log, P=0.002 by ANOVA) compared with BCG and the differences were statistically significant.

Example 5

Antibody to Purified Recombinant *M. tuberculosis* 30 kDa Major Protein (r30)

Blood is obtained from the animals described above immediately after they are euthanized, and the serum is assayed for antibody titer to r30 by ELISA, using Costar (Corning, N.Y.) 96-well EIA/RIA High Binding Plates, r30 at 1 μg/well, guinea pig serum diluted 1:64 to 1:1,024,000, alkaline phosphatase-conjugated goat anti-guinea pig IgG (Sigma, St. Louis, Mo.) at a dilution of 1:1,000, and an Alkaline Phosphatase Substrate Kit (BioRad, Hercules, Calif.).

Example 6

Lymphocyte Proliferation

Three weeks after immunization, animals are euthanized and the spleen removed for lymphocyte proliferation studies. Splenic lymphocytes are purified as described (Pal and Horwitz, Infect. Immun. 60:4781-4792, 1992) and incubated at a final concentration of $10^7$/ml in RPMI1640 containing 12.5 mM HEPES, penicillin (100 U/ml), streptomycin (100 μg/ml), polymyxin B sulfate (100 Units/ml), and 10% fetal calf serum (Gibco) with PPD (10 mg/ml) or with 100, 10, or 1 μg/ml of purified *M. tuberculosis* 30 kDa major secretory protein (r30) in a total volume of 100 μl in microtest wells (96-well round-bottom tissue culture plate; Falcon Labware, Oxnard, Calif.) for 2 days at 37° C. in 5% $CO_2$-95% air and 100% humidity. As negative and positive controls, lymphocytes sre incubated with buffer only (RPMI) or with concanavalin A (15 μg/ml). Subsequently, [$^3$H]thymidine incorporation is determined and mean Counts Per Minute (CPM) calculated. Stimulation Indices (SI) are calculated using the following formula: SI=CPM with Antigen/CPM without Antigen.

Lymphocytes from animals immunized with BCG have a weak proliferative response to r30, but a moderately strong response to PPD. In contrast, lymphocytes from animals immunized with rBCG expressing the 30 kDa protein have a strong proliferative response to both r30 and PPD.

REFERENCES

Agarwal, N., and Tyagi, A. K. (2003). Role of 5'-TGN-3' motif in the interaction of mycobacterial RNA polymerase with a promoter of 'extended-10' class. FEMS Microbiol Lett 225, 75-83.

Arndt, K. M., and Chamberlin, M. J. (1988). Transcription termination in *Escherichia coli*. Measurement of the rate of enzyme release from Rho-independent terminators. J Mol Biol 202, 271-285.

Arnvig, K. B., Pennell, S., Gopal, B., and Colston, M. J. (2004). A high-affinity interaction between NusA and the rrn nut site in *Mycobacterium tuberculosis*. Proc Natl Acad Sci USA 101, 8325-8330.

Bardarov, S., Bardarov Jr, S., Jr., Pavelka Jr, M. S., Jr., Sambandamurthy, V., Larsen, M., Tufariello, J., Chan, J., Hatfull, G., and Jacobs Jr, W. R., Jr. (2002). Specialized transduction: an efficient method for generating marked and unmarked targeted gene disruptions in *Mycobacterium tuberculosis, M. bovis* BCG and *M. smegmatis*. Microbiology 148, 3007-3017.

Cardenas, L., and Clements, J. D. (1993). Stability, immunogenicity and expression of foreign antigens in bacterial vaccine vectors. Vaccine 11, 126-135.

Gentz, R., Langner, A., Chang, A. C., Cohen, S. N., and Bujard, H. (1981). Cloning and analysis of strong promoters is made possible by the downstream placement of a RNA termination signal. Proc Natl Acad Sci USA 78, 4936-4940.

Gumbiner-Russo, L. M., Lombardo, M. J., Ponder, R. G., and Rosenberg, S. M. (2001). The TGV transgenic vectors for single-copy gene expression from the *Escherichia coli* chromosome. Gene 273, 97-104.

Hone, D., Attridge, S., van den Bosch, L., and Hackett, J. (1988). A chromosomal integration system for stabilization of heterologous genes in *Salmonella* based vaccine strains. Microb Pathog 5, 407-418.

Hoover, D. M., and Lubkowski, J. (2002). DNAWorks: an automated method for designing oligonucleotides for PCR-based gene synthesis. Nucleic Acids Res 30, e43.

Horwitz, M. A., Harth, G., Dillon, B. J., and Maslesa-Galic, S. (2000). Recombinant *bacillus* calmette-guerin (BCG) vaccines expressing the *Mycobacterium tuberculosis* 30-kDa major secretory protein induce greater protective immunity against tuberculosis than conventional BCG vaccines in a highly susceptible animal model. Proc Natl Acad Sci USA 97, 13853-13858.

Howard, N. S., Gomez, J. E., Ko, C., and Bishai, W. R. (1995). Color selection with a hygromycin-resistance-based *Escherichia coli*-mycobacterial shuttle vector. Gene 166, 181-182.

Ma, J., Campbell, A., and Karlin, S. (2002). Correlations between Shine-Dalgarno sequences and gene features such as predicted expression levels and operon structures. J Bacteriol 184, 5733-5745.

McKenzie, G. J., and Craig, N. L. (2006). Fast, easy and efficient: site-specific insertion of transgenes into enterobacterial chromosomes using Tn7 without need for selection of the insertion event. BMC Microbiol 6, 39.

Postle, K., and Good, R. F. (1985). A bidirectional rho-independent transcription terminator between the *E. coli* tonB gene and an opposing gene. Cell 41, 577-585.

Schollmeier, K., Gartner, D., and Hillen, W. (1985). A bidirectionally active signal for termination of transcription is located between tetA and orfL on transposon Tn10. Nucleic Acids Res 13, 4227-4237.

Spreng, S., and Viret, J. F. (2005). Plasmid maintenance systems suitable for GMO-based bacterial vaccines. Vaccine 23, 2060-2065.

Telesnitsky, A., and Chamberlin, M. J. (1989). Terminator-distal sequences determine the in vitro efficiency of the early terminators of bacteriophages T3 and T7. Biochemistry 28, 5210-5218.

Tullius, M. V., Harth, G., and Horwitz, M. A. (2001). High extracellular levels of *Mycobacterium tuberculosis* glutamine synthetase and superoxide dismutase in actively growing cultures are due to high expression and extracellular stability rather than to a protein-specific export mechanism. Infect Immun 69, 6348-6363.

Verma, A., Kinger, A. K., and Tyagi, J. S. (1994). Functional analysis of transcription of the *Mycobacterium tuberculosis* 16S rDNA-encoding gene. Gene 148, 113-118.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An immunogenic composition comprising a recombinant Bacille Calmette Guérin (BCG) wherein said recombinant BCG expresses at least one *Mycobacteria major* extracellular protein selected from 23.5 kDa protein, 30 kDa protein, 32A kDa protein, and 32B kDa protein; wherein a nucleic acid sequence encoding for said at least one *Mycobacteria major* extracellular protein is incorporated into said recombinant BCG's chromosome(s) under a strong promoter such that said *Mycobacteria major* extracellular protein is over-expressed, and the recombinant BCG does not harbor an antibiotic resistance marker.

2. The immunogenic composition of claim 1 wherein said least one *Mycobacteria major* extracellular protein is from *Mycobacterium bovis, M. tuberculosis, M. leprae, M. kansasii, M. avium*, or *Mycobacterium* sp.

3. The immunogenic composition according to claim 1 wherein said recombinant BCG is growth regulatable.

4. The immunogenic composition according to claim 2 wherein said recombinant BCG further expresses at least one *Mycobacteria major* extracellular protein selected from 12 kDa protein, 14 kDa protein, 16 kDa protein, 24 kDa protein, 45 kDa protein, 58 kDa protein, 71 kDa protein, 80 kDa protein, and 110 KD protein.

5. The immunogenic composition according to claim 1 further comprising at least one cytokine, wherein the cytokine is interferon gamma, interleukin-2, interleukin-12, soluble interleukin-4 receptor, and granulocyte macrophage colony stimulating factor, or combinations thereof.

6. The immunogenic composition according to claim 1 wherein said promoter is the promoter for a *M. tuberculosis* rrs gene or a shortened derivative thereof.

* * * * *